(12) United States Patent
Meier et al.

(10) Patent No.: US 9,549,752 B2
(45) Date of Patent: Jan. 24, 2017

(54) ULTRASONIC SURGICAL INSTRUMENT

(71) Applicant: Söring GmbH, Quickborn (DE)

(72) Inventors: Markus Meier, Quickborn (DE);
Florian Neumann, Hamburg (DE);
Hendrik Hagedorn, Delmenhorst (DE)

(73) Assignee: Soring GmbH, Quickborn (DE)

( * ) Notice: Subject to any disclaimer, the term of this patent is extended or adjusted under 35 U.S.C. 154(b) by 96 days.

(21) Appl. No.: 14/358,343

(22) PCT Filed: Nov. 14, 2012

(86) PCT No.: PCT/EP2012/072599
§ 371 (c)(1),
(2) Date: May 15, 2014

(87) PCT Pub. No.: WO2013/072357
PCT Pub. Date: May 23, 2013

(65) Prior Publication Data
US 2015/0190167 A1    Jul. 9, 2015

(30) Foreign Application Priority Data
Nov. 15, 2011  (DE) ........................ 10 2011 086 326

(51) Int. Cl.
*A61B 17/32* (2006.01)
*A61B 17/29* (2006.01)

(52) U.S. Cl.
CPC .................. *A61B 17/320068* (2013.01); *A61B 2017/2904* (2013.01); *A61B 2017/320084* (2013.01);
(Continued)

(58) Field of Classification Search
CPC ........... A61B 17/320068; A61B 2017/320084; A61B 2017/320088; F16F 15/00; F16F 15/02
(Continued)

(56) References Cited

U.S. PATENT DOCUMENTS 3,671,887 A    6/1972  Gibson
4,315,181 A    2/1982  Holze, Jr.
(Continued)

FOREIGN PATENT DOCUMENTS

JP    S62298346 A    12/1987
JP    03146047 A2    6/1991
(Continued)

OTHER PUBLICATIONS

International Preliminary Report on Patentability dated May 20, 2014 (PCT/EP2012/072599).
(Continued)

*Primary Examiner* — Thomas McEvoy
(74) *Attorney, Agent, or Firm* — Alix, Yale & Ristas, LLP

(57) ABSTRACT

The invention relates to an ultrasonic surgical instrument with a support structure (20), and with an ultrasonic transducer (17) suspended on the support structure (20). A sonotrode (16) is connected to the ultrasonic transducer (17). The support structure (20) comprises a jacket portion (24) that extends around an inner space. According to the invention, the ultrasonic transducer (17) is suspended on a retaining ring (21), which is arranged in a continuation of the jacket portion (24) and which is connected to the jacket portion (24) via a connecting section (23). The connecting portion (24) has a plurality of apertures (26, 27) which in total cover the whole circumference of the connecting portion (24). The invention has the advantage that the
(Continued)

instrument is uncoupled from the oscillations of the ultrasonic transducer.

19 Claims, 2 Drawing Sheets

(52) U.S. Cl.
CPC ............. *A61B 2017/320088* (2013.01); *F04C 2270/0421* (2013.01)

(58) Field of Classification Search
USPC .................................................. 267/136, 137
See application file for complete search history.

(56) References Cited

U.S. PATENT DOCUMENTS

| | | |
|---|---|---|
| 4,681,561 A | 7/1987 | Hood et al. |
| 4,816,017 A | 3/1989 | Hood et al. |
| 5,057,119 A | 10/1991 | Clark et al. |
| 5,526,815 A | 6/1996 | Granz et al. |
| 5,626,560 A | 5/1997 | Soring |
| 5,921,999 A | 7/1999 | Dileo |
| 6,551,337 B1 | 4/2003 | Rabiner et al. |
| 2003/0125645 A1 | 7/2003 | Rabiner et al. |
| 2004/0037626 A1* | 2/2004 | Awtar ..................... F16C 11/12 403/223 |
| 2005/0020966 A1 | 1/2005 | Soring et al. |
| 2009/0030437 A1* | 1/2009 | Houser .......... A61B 17/320092 606/169 |
| 2011/0196405 A1* | 8/2011 | Dietz ............. A61B 17/320068 606/169 |
| 2012/0049422 A1* | 3/2012 | Gnateski ................ F16F 1/028 267/140.13 |
| 2012/0204550 A1* | 8/2012 | Al-Bender ............ F16F 15/005 60/420 |

FOREIGN PATENT DOCUMENTS

| | | |
|---|---|---|
| JP | 05031118 A2 | 2/1993 |
| JP | 06133981 A2 | 5/1994 |
| JP | 10127653 A2 | 5/1998 |
| JP | 2001079012 A2 | 3/2001 |
| WO | 2004021404 A2 | 3/2004 |

OTHER PUBLICATIONS

International Search Report dated Sep. 30, 2013 (PCT/EP2012/072599).

* cited by examiner

ULTRASONIC SURGICAL INSTRUMENT

BACKGROUND

The invention relates to an ultrasonic surgical instrument, in which an ultrasonic transducer is suspended on a support structure. A sonotrode is connected to the ultrasonic transducer. The support structure comprises a cladding section, which encloses an interior.

During surgery, such an ultrasonic surgical instrument can be used to sever tissue. The ultrasonic transducer makes the sonotrode undergo high-frequency vibrations. A front end of the sonotrode is brought into contact with the tissue such that the vibrations act on the tissue and the tissue is severed.

Since the ultrasonic transducer is connected not only to the sonotrode but also to the support structure, it can also make the support structure vibrate. This is undesirable since this places an unnecessary load onto the instrument and the handling becomes more difficult.

SUMMARY

The invention is based on the object of presenting an ultrasonic surgical instrument, in which vibrations transmitted from the ultrasonic transducer to the support structure are reduced. Proceeding from the prior art set forth at the outset, the object is achieved by the features of claim 1. Advantageous embodiments are found in the dependent claims.

According to the invention, the ultrasonic transducer is suspended on a retaining ring. The retaining ring is arranged in a continuation of the cladding section and connected to the cladding section by means of a connection section. The connection section is provided with a plurality of perforations, which, overall, cover the whole circumference of the connection section.

A few terms will be explained first. The direction in which the cladding section, the connection section and the retaining ring are arranged in succession is referred to as longitudinal direction. The interior enclosed by the cladding section extends through the cladding section, the connection section and the retaining ring in the longitudinal direction.

If a plurality of perforations, overall, cover the whole circumference of the connection section, this means that the perforations would form a continuous perforation extending over the whole circumference of the connection section if the perforations were to be projected onto a common position in the longitudinal direction. According to the invention, the perforations are arranged at different longitudinal positions, and so there are connecting webs between the perforations, which connecting webs establish the connection between the cladding section and the retaining ring. The support structure containing the cladding section, the connection section and the retaining ring preferably has an integral embodiment.

The invention has identified that the connection section provided with perforations can decouple the vibrations in the longitudinal direction. If the ultrasonic transducer generates a vibration in the longitudinal direction, this vibration is transferred to the retaining ring, on which the ultrasonic transducer is suspended. A transfer of the vibrations from the retaining ring to the cladding section is prevented by the perforations. Thus, the cladding section and the part of the support structure adjoining this remain at rest, even though the ultrasonic transducer generates high-frequency vibrations and transmits these to the sonotrode. By contrast, the connection section is rigid in relation to pressure forces in the lateral direction and in relation to torsional forces, and so these forces can be reliably transmitted.

So that the instrument overall can remain compact, it is desirable to keep the extent of the connection section small in the longitudinal direction. This can be achieved by virtue of providing a plurality of perforations, which have a large extent in the circumferential direction and a small extent in the longitudinal direction. The extent in the circumferential direction is preferably at least twice as big, more preferably at least five times as big, more preferably at least ten times as big, as the extent in the longitudinal direction.

It is advantageous for decoupling the vibrations if there is no direct and continuous connection between the retaining ring and the cladding section in the longitudinal direction. Provision can therefore be made for an overlap between a first perforation and, adjoining this in the circumferential direction, a second perforation. Consequently, the first perforation and the second perforation follow one another in the longitudinal direction in the region of the overlap. Preferably, an overlap is provided at each transition from one perforation to the next perforation.

In order to keep the extent of the connection section small in the longitudinal direction, it is moreover advantageous if the spacing between the first perforation and the second perforation in the region of the overlap is less than the width of the perforations.

In order to be able to connect the ultrasonic transducer with the retaining ring, the retaining ring can have a fastening element. There regularly are a plurality of fastening elements, which are distributed evenly over the circumference of the retaining ring. Provision can be made for perforations which are guided around the fastening elements. If a perforation is guided around a fastening element, this means that a first section of the perforation is situated closer to the cladding section than a second section of the perforation. The fastening element is arranged in the region next to the first section. Overall, a perforation which is guided around a fastening element should also extend substantially in the circumferential direction.

Good decoupling of the vibrations is achieved if a plurality of perforations are distributed over the circumference of the connection section in such a way that the end sections of the perforations lie against one another head-to-head and are merely separated by a connecting web. Two further perforations, which extend parallel to one another, can enclose these end sections between them. Labyrinthine connecting webs which have good resilient properties are formed in this manner.

The extent of the cladding section in the longitudinal direction need not be large. The cladding section merely needs to be so stable that it can offer the ultrasonic transducer support by means of the connection section and the retaining ring. A housing, which can serve to hold components such as the ultrasonic transducer, can adjoin the cladding section. The ultrasonic transducer is preferably arranged in the interior. The housing can be provided with an opening for supplying a rinsing fluid to the front end of the instrument. Additionally, or as an alternative thereto, provision can be made in the housing for an opening through which liquids from the front end of the instrument can be sucked away. The front end refers to the region of the instrument which serves to treat the tissue.

The rear end of the instrument can be configured as a handle, which is held by the surgeon when using the instrument. The cladding section can be provided with a connection element, by means of which the handle can be connected to the support structure. By way of example, the connection element can be a thread arranged around the circumference of the cladding section.

At the front end of the support structure, provision can be made for a connection element for connecting a sleeve, through which the sonotrode extends. The sleeve can also be connected to the support structure via a thread. In an advantageous embodiment, the support structure has a knee-like design, such that the sleeve is angled with respect to the handle.

If the ultrasonic transducer generates a vibration in the longitudinal direction, the amplitude of the vibration differs depending on which section of the vibrating system is considered. There is a transition region, in which the amplitude of the vibration is very small, between two counter-vibrating sections. This transition region is referred to as node of the vibration. The ultrasonic transducer is preferably suspended in the node of the vibration. An advantage of this is that the vibrations, which can be transferred to the support structure, are minimized from the outset. The damping according to the invention can be restricted to catch the residual remainder of the vibration.

BRIEF DESCRIPTION OF THE DRAWINGS

With reference to the attached drawings, the invention will be described in an exemplary manner hereinbelow on the basis of advantageous embodiments. In detail.

DETAILED DESCRIPTION

Figure 1:
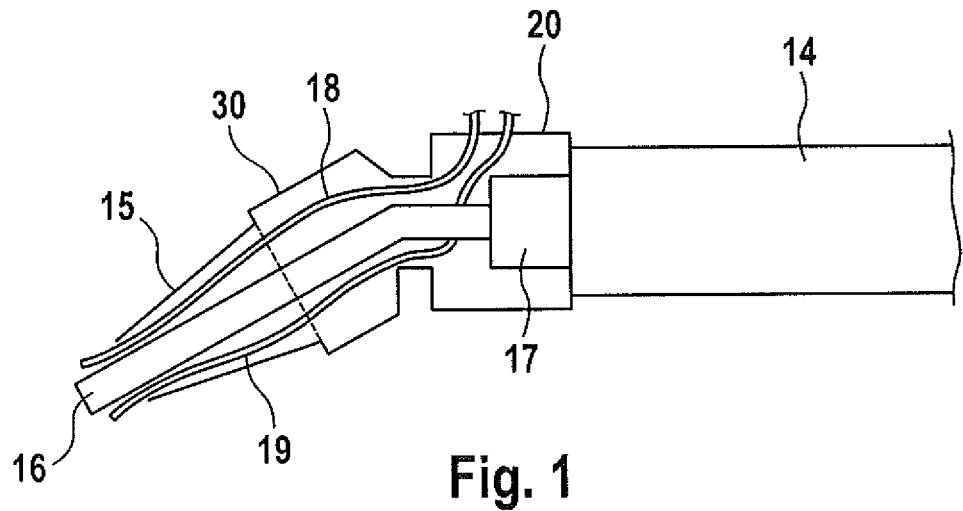
FIG. 1 shows a schematic sectional illustration of an ultrasonic surgical instrument according to the invention.

An ultrasonic surgical instrument in FIG. 1 comprises a handle 14 at its rear end, which the surgeon can grip when he uses the instrument. At the front end thereof, the instrument has a sleeve 15, through which a sonotrode 16 is guided, the end of which projects forward beyond the sleeve 15. The rear end of the sonotrode 16 is connected to an ultrasonic transducer 17. The ultrasonic transducer 17 receives an electric AC voltage signal with an ultrasonic frequency as input signal, which is generated by a signal generator not depicted in FIG. 1. The ultrasonic transducer comprises a piezoelectric element, by means of which the electric signal is converted into a mechanical vibration. The mechanical vibration is transferred to the sonotrode 16. Using the front end of the sonotrode 16, the vibration can be transferred to the tissue of a patient, in order to sever the latter.

A line 18 is guided to the front end of the instrument so as to be able to supply a rinsing fluid to the operating field. A second line 19 serves to suck liquids away from the operating field.

The instrument moreover comprises a knee 20, which forms a support structure of the instrument. The ultrasonic transducer 17 is suspended on the knee 20; the handle 14 is connected to the rear end of the knee 20 and the sleeve 15 is connected to the front end of the knee. The knee 20 is integral and can consist of e.g. stainless steel.

Figure 2:
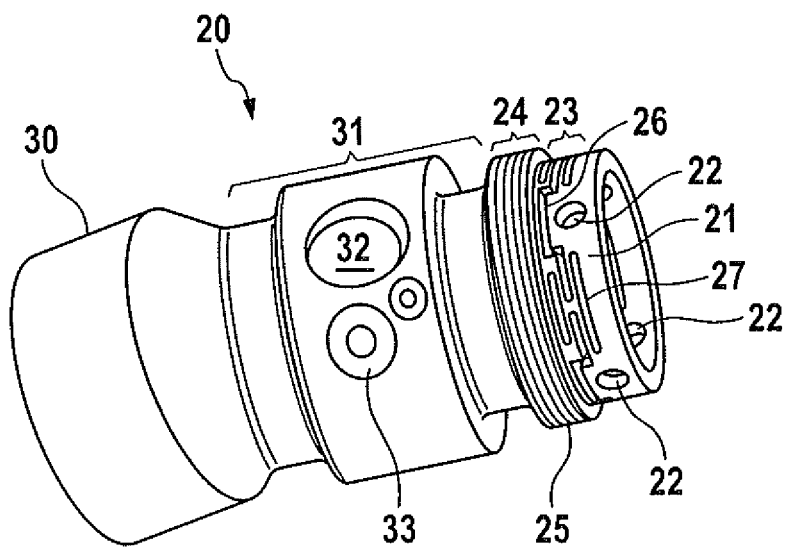
FIG. 2 shows a magnified illustration of the knee from FIG. 1.

FIG. 2 shows the knee 20 in a magnified illustration.

The knee 20 comprises a retaining ring 21, on which the ultrasonic transducer 17 is suspended. The retaining ring 21 is provided with four bores 22, which form fastening elements for the ultrasonic transducer 17. The connection is established by means of screws, which are guided in through the bores 22. The retaining ring 21 is connected to a cladding section 24 by means of a connection section 23. On the circumference thereof, the cladding section 24 is provided with a thread 25, by means of which the handle 14 can be connected to the knee 20. The retaining ring 21 is positioned in such a way that the vibration transducer is suspended in the node of the vibration.

When the ultrasonic transducer 17 is in operation, the vibrations are transferred not only to the sonotrode 16 but also to the retaining ring 21, which is rigidly connected to the ultrasonic transducer 17. The connection section 23 serves to avoid a transfer of the vibrations from the retaining ring 21 to the cladding section 24. Otherwise, the whole instrument would be put into vibration by the cladding section 24.

Figure 3:
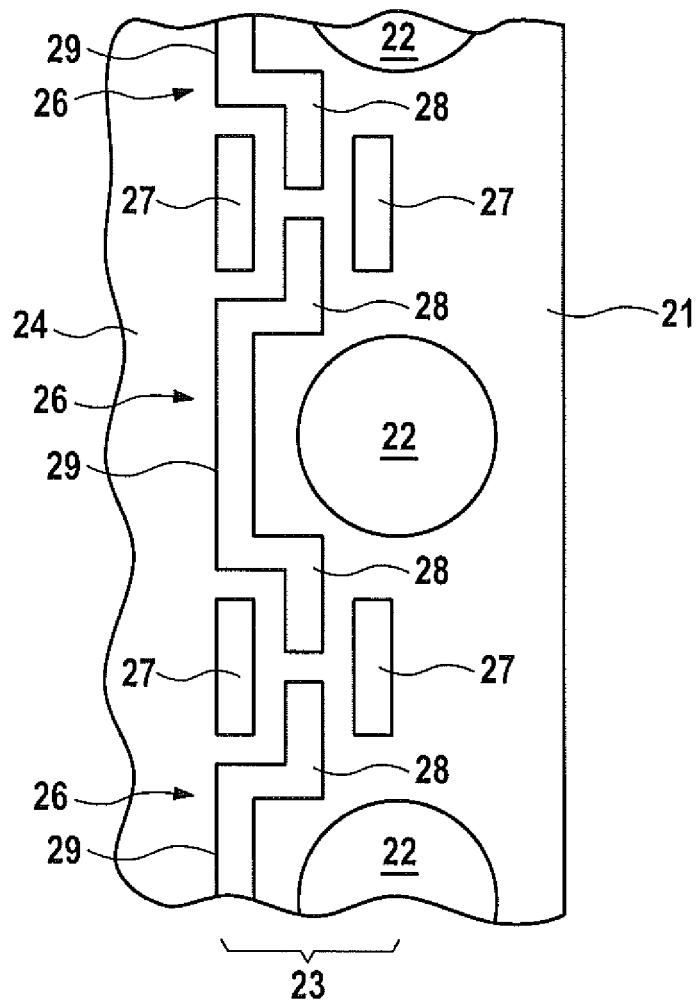
FIG. 3 shows a magnified illustration of the connection section of the knee from FIG. 2.

In order to impart the effect of a spring element, which decouples the vibrations of the retaining ring 21 from the cladding section 24, to the connection section 23, the connection section 23 is provided with perforations 26, 27. In FIG. 3, in which the circumference of the knee 20 is projected into the plane, the perforations 26, 27 are depicted in a magnified manner. Accordingly, there is a perforation 26 for each of the four bores 22, which perforation is guided around the bore 22. The perforations 26 each have two end sections 28, which are aligned in the circumferential direction and positioned in the longitudinal direction in such a way that they intersect the bores 22 if they are continued. The perforations 26 are guided around the bores 22 by virtue of comprising a central section 29, which is displaced in parallel to the end sections 28 and is situated closer to the cladding section 24. The central sections 29 provide the option of moving the bores 22 closer to the cladding section 24, and so the knee 20 overall has a compact embodiment.

Further perforations 27, which are arranged parallel to one another and which enclose the end sections 28 therebetween, are formed in the region of the end sections 28. Thus, there is an overlap between the perforations 27 and each of the end sections 28.

There are connecting webs between the perforations 27 and the perforations 28, which webs extend in a labyrinthine manner between the retaining ring 21 and the cladding section 24. The connecting webs form an elastic connection between the retaining ring 21 and the cladding section 24 such that the vibrations transmitted to the retaining ring 21 are not transferred.

At the front end thereof, the knee 20 comprises a flange 30, which is angled with respect to the cladding section 24. The flange 30 comprises a thread (not visible in FIG. 2), into which the sleeve 15 can be screwed. A housing section 31, in the interior of which the ultrasonic transducer is held, extends between the flange 30 and the cladding section 24. The housing section 31 is provided with openings 32, 33, through which the lines 18, 19 can be guided.

The invention claimed is:

1. An ultrasonic surgical instrument comprising an ultrasonic transducer (17) suspended on a support structure (20) and a sonotrode (16) connected to said ultrasonic transducer, the support structure (20) having a cladding section (24) extending around an interior, wherein the ultrasonic transducer (17) is suspended on a retaining ring (21), which is arranged in a continuation of the cladding section (24) and connected to the cladding section (24) via a longitudinally intermediate connection section (23) integrally connected to the retaining ring (21), the connection section defining a plurality of perforations (26, 27), which collectively angularly span the entire circumference of the connection section (23), wherein said support structure has the following order of arrangement in a proximal to distal direction relative to an operator: retaining ring, connecting section and cladding section.

2. The instrument of claim 1, wherein the circumferential length of each of the plurality of perforations (26, 27) is at least approximately twice the length of each of the plurality of perforations (26, 27) in the longitudinal direction.

3. The instrument of claim 1, comprising a first perforation (26) and a second perforation (27) spaced longitudinally from each other, wherein the first perforation (26) and second perforation (27) overlap in the circumferential direction.

4. The instrument of claim 3, wherein the first perforation (26) and second perforation (27) are longitudinally spaced a distance that is less than the longitudinal width of the perforations.

5. The instrument of claim 1, comprising a perforation (26) that is guided around a fastening element (22) for the ultrasonic transducer (17).

6. The instrument of claim 1, wherein two perforations (27) extend parallel to each other on opposite longitudinal sides of end sections (28) of two further perforations (26).

7. The instrument of claim 6, wherein the two perforations (27) and end sections (28) extend circumferentially substantially parallel to each other.

8. The instrument of claim 1, comprising a housing section (31) that encloses the interior and adjoins the cladding section.

9. The instrument of claim 8, wherein the housing section (31) includes one or more of an opening (32) for supplying a rinsing fluid to the interior and an opening (33) for removing fluid from the interior.

10. The instrument of claim 1, wherein the ultrasonic transducer (17) is positioned in the interior.

11. The instrument of claim 1, wherein the ultrasonic transducer (17) is suspended in a position longitudinally between two counter-vibrating structures in a position of reduced vibration.

12. The instrument of claim 1, wherein the cladding section (24) is provided with a connection element (25) for a handle (14).

13. An ultrasonic surgical instrument comprising an ultrasonic transducer (17) suspended on a support structure (20) and a sonotrode (16) connected to said ultrasonic transducer, the support structure (20) defining a central axis and having a cladding section (24) extending around an interior, wherein the ultrasonic transducer (17) is suspended on a retaining ring (21) longitudinally removed from the cladding section (24) with an intermediate connection section (23) transitioning the cladding section (24) to the retaining ring (21), the connection section (23) integrally connected to the retaining ring (21) and defining a plurality of longitudinally and circumferentially spaced perforations (26, 27) extending about the circumference and a handle fixedly (14) mounted to the cladding section.

14. The instrument of claim 13, wherein the cladding section (24), connection section (23) and retaining ring (21) are formed as a single unit.

15. The instrument of claim 13, wherein the plurality of longitudinally and circumferentially spaced perforations (26, 27) collectively angularly span the entire circumference of the support structure.

16. The instrument of claim 13, wherein the plurality of perforations (26, 27) are defined in the connection section (23) only.

17. The instrument of claim 13, wherein at least one of the perforations (26) comprises a pair of longitudinally spaced circumferentially extending segments (28, 29) connected via an intermediate segment.

18. The instrument of claim 17, wherein the intermediate segment extends substantially perpendicular to the pair of longitudinally extending segments (28, 29).

19. The instrument of claim 13, wherein a pair of the perforations (26, 27) extends circumferentially parallel to each other with at least a segment (28) of at least one additional perforation positioned longitudinally therebetween.

* * * * *